United States Patent [19]

Kuris

[11] 4,192,035

[45] Mar. 11, 1980

[54] ULTRASONIC TOOTHBRUSH

[75] Inventor: Arthur Kuris, Riverdale, N.Y.

[73] Assignee: Ultrasonic Plaque Control Laboratories, Inc., New York, N.Y.

[21] Appl. No.: 958,663

[22] Filed: Nov. 8, 1978

[51] Int. Cl.² .............................................. A46B 13/02
[52] U.S. Cl. .................................. 15/22 R; 128/62 A; 318/116
[58] Field of Search ................... 15/22 R, 22 A, 22 B; 128/62 A; 318/116, 118; 32/58

[56] References Cited

U.S. PATENT DOCUMENTS

| | | | |
|---|---|---|---|
| 3,335,443 | 8/1967 | Parisi et al. | 15/22 R |
| 3,375,820 | 4/1968 | Kuris et al. | 128/62 A |
| 3,809,977 | 5/1974 | Balamuth et al. | 318/116 |
| 3,828,770 | 8/1974 | Kuris et al. | 128/62 A |
| 3,840,932 | 10/1974 | Balamuth et al. | 15/22 R X |
| 3,941,424 | 3/1976 | Balamuth et al. | 15/22 R X |

Primary Examiner—Edward L. Roberts
Attorney, Agent, or Firm—Leonard W. Suroff

[57] ABSTRACT

Apparatus for use in personal dental hygiene care comprising an elongated member formed at least in part of a piezoelectric member with a pair of contacting surfaces intermediate the respective ends thereof with a brush member adapted to be received within the human mouth and moved across tooth and gingival surfaces and extending from one end of the elongated member. A casing adapted to be held in the hand is provided and is of a length at least equal to the piezoelectric member and having an elongated bore adapted to receive the piezoelectric member of the elongated member therein. Sealing means in the bore to engage the elongated member in readily releasable and in a fluid-tight fashion is used. Electrical contact means contained in the casing for releasable engagement with the contacting surfaces of the piezoelectric member of the elongated member is utilized so as to obtain electrical contact upon the insertion of the elongated member within the bore and disengagement of the electrical contact means upon removal from the bore of the elongated member. Generating means to supply alternating electrical signals to the contact means to establish an alternating field for transmission from the contact means to the piezoelectric member is provided whereby mechanical vibrations at the frequency of the alternating signals are induced in the elongated member and the brush member.

28 Claims, 5 Drawing Figures

ULTRASONIC TOOTHBRUSH

BACKGROUND OF THE INVENTION

1. Field of the Invention

The present invention relates to apparatus for the cleaning of teeth and more particularly to an apparatus for personal dental care employing ultrasonic energy suitable for regular use in the home for oral hygiene.

Accordingly, with periodic examination and treatment by professionally trained dentists, it has been established that significant benefits are derived from regular dental care performed in the home by the individual himself. It is universally recognized, for example, that regular brushing of the teeth, particularly after every meal, serves to dislodge food particles which ordinarily are retained adjacent the teeth and which, if allowed to remain, would cause decay and dental caries. When properly administered, regular brushing also serves to maintain good circulation in gingival tissue, thereby lessening the likelihood of gingival disease, one of the prime causes of premature loss of teeth. Perhaps of less, but nevertheless significant, importance are the stain removal and brightening actions resulting from regular brushing, which contribute noticeably to the appearance of the individual.

The present invention has found that, when applied under proper control to tooth and gingival surfaces in the human mouth, ultrasonic energy may be successfully employed for regular oral hygienic care without any damage to tooth surfaces or gingival tissues. These ultrasonic cleaning techniques provide a significantly increased cleaning ability, particularly in the interproximal and gum line areas where presently known brushing techniques are inadequate. Briefly, in accordance with the present invention, a cleaning member, which preferably includes a plurality of individual cleaning elements, such as the bristles on a brush, is vibrated at an ultrasonic rate and manually moved over tooth and gingival surfaces under relatively light pressure.

Although not necessarily limited thereto, the combined ultrasonic and manual movement of the cleaning member may be performed in the presence of a fluid, such as water added specifically for the purpose, or the natural fluids present in the human mouth and in the presence of the usual dentifrices such as toothpaste and tooth powder. The unique properties displayed at the tips of an ultrasonically vibrating member such as a brush, enable greatly improved cleaning results to be achieved, particularly in areas where manual or conventional motor driven toothbrushes cannot reach. The ultrasonic energy is applied to the tooth and gingival surfaces such that no damage whatsoever to the surfaces will result. On the other hand, because of the greatly improved cleaning power, the buildup of tartar and scale deposits in the interproximal and subgingival areas is significantly lessened, promoting a much higher degree of dental health than is possible with ordinary methods of dental hygienic care.

2. Discussion of the Prior Art

The prior art has attempted to solve the problem of utilizing ultrasonic mechanical vibratory energy for the cleaning of teeth and has approached the problem in a number of directions which the present inventor believes should be discussed herein in order to clearly define the novelty associated with the present invention, the details of which will be hereinafter discussed.

One approach to the cleaning of teeth, as well as other surfaces, has been the utilization of bristles vibrated in a manner to remove foreign deposits, plaque, and other surface materials that normally adhere to teeth within the human body. Certain patents representative of the utilization of bristles for the cleaning of teeth are contained in U.S. Pat. Nos. 3,335,443; 3,375,820; 3,488,788; 3,535,726; 3,593,425; 3,676,218; 3,809,977; 3,828,770; Re 28,752; 3,139,109; 3,166,772; 3,840,932; 3,941,424; and 4,012,647. The above body of prior art as contained in the above referenced patents, the subject of which is incorporated herein, is believed to be sufficiently representative of those patents which disclose bristle elements brought into substantial engagement with the teeth in conjunction with a fluid film to assist the cavitational action or frictional engagement between the free ends of the bristles to remove the material.

What has occurred to date is that notwithstanding the teaching of the prior art, the ability to obtain a quick interchange of the brush element from user to user has remained to a great extent unsolved, and therefore proper cleaning action was not always attainable in a commercially acceptable appliance.

In contrast to the above body of prior art teaching, there has also developed a number of applications embodied in U.S. Patents which primarily have only fluid as the medium for the transmission of the vibratory energy to the surface of the teeth. These patents are U.S. Pat. Nos. 3,380,446; 3,401,690; 3,522,801; 3,547,110; 3,636,947; 3,760,799; and 3,847,662, the subject matter of which is incorporated herein by reference.

The present inventor has found that it is most impractical to have a user retain in one's mouth a moulded element and have fluid pumped therein with the intention of obtaining cavitational action at a level sufficient to obtain the cleaning of the foreign material as taught by the above body of prior art patents.

Accordingly, in view of the above the present invention provides for a toothbrush to be used by the consumer having interchangeable elements that may be readily inserted within the handpiece and immediate electrical contact is made for powering of the ultrasonic motor forming a part thereof. In this manner a simple and efficient instrument is obtained having superior qualities over that disclosed in the prior art.

OBJECTS OF THE INVENTION

An object of the present invention is to provide a new and novel apparatus for the cleaning of surfaces such as teeth that may be within the mouth or may be in the form of dentures.

Another object of the present invention is to provide an ultrasonic system for regular personal oral hygienic care giving excellent cleaning results in the hard to reach interproximal and gum line areas and in general, in areas around the teeth that are normally relatively inaccessible.

Another object of the present invention is to provide a novel form of apparatus employing ultrasonic energy for use in regular personal oral hygienic care in which the cleaning element or brush itself is readily replaceable, thereby enabling a single power handle to be used with a plurality of cleaning elements.

Another object of the present invention is to provide an improved apparatus for regular personal oral hygienic care, employing ultrasonic energy, in which the cleaning element is readily replaceable.

Other objects and advantages of the invention will become apparent as the disclosure proceeds.

SUMMARY OF THE INVENTION

The apparatus of the present invention is for use in personal dental hygiene care and includes an elongated member formed at least in part of a piezoelectric member with a pair of contacting surfaces intermediate the respective ends thereof. A brush member adapted to be received within the human mouth and moved across tooth and gingival surfaces extends from one end of the elongated member and includes a plurality of bristles.

A casing adapted to be held in the hand and of a length at least equal to the piezoelectric member and having an elongated bore adapted to receive the piezoelectric member of the elongated member therein is provided. The casing may include an outer casing member with an inner casing member adapted to extend in telescopic relation within the outer casing for retainment of the contact means thereon. Mounting means is provided for retaining the inner casing within the outer casing in fixed position thereto.

Sealing means is provided in the bore to engage the elongated member in readily releasable and in a fluid-tight fashion. Electrical contact means is contained in the casing for releasable engagement with the contacting surfaces of the piezoelectric member of the elongated member, so as to obtain electrical contact upon the insertion of the elongated member within the bore and disengagement of the electrical contact means upon removal from the bore of the elongated member.

The contact means may include a pair of oppositely disposed contact members mounted in the bore, and each contact member has a coupling surface for engagement with one of the contacting surfaces. The contact members each include a body portion and an arm extending from each end of the body portion and rigidly coupled to the casing by means of fasteners. If desired there may also be provided friction reduction means operatively associated with each one of the contact members so as to facilitate the insertion and removal of the elongated member within the bore. The friction reduction means may include at least one metallic roller mounted on each one of the contact members to maintain electrical transmission between the generating means and the piezoelectric member. The body portion would then include a pair of flanges with an opening therebetween and each roller is mounted in a plane perpendicular to the axis of the bore within the opening.

Generating means to supply alternating electrical signals to the contact means to establish an alternating field for transmission from the contact means to the piezoelectric member is provided whereby mechanical vibrations at the frequency of the alternating signals are induced in the elongated member and the brush member. The generating means may be contained in a housing with a pair of electrical prongs extending therefrom and adapted to be plugged into a wall outlet for powering same with switch means adapted to be engaged by a user for powering same and extending from the housing or on the casing, as desired.

The apparatus may also include guide means to provide an indication for the user as to the correct positionment of the elongated member within the bore to obtain proper engagement between the contacting surfaces and the contact means. The guide means may include indicia on the elongated member and casing.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DETAILED DESCRIPTION OF THE DRAWINGS

Figure 1:
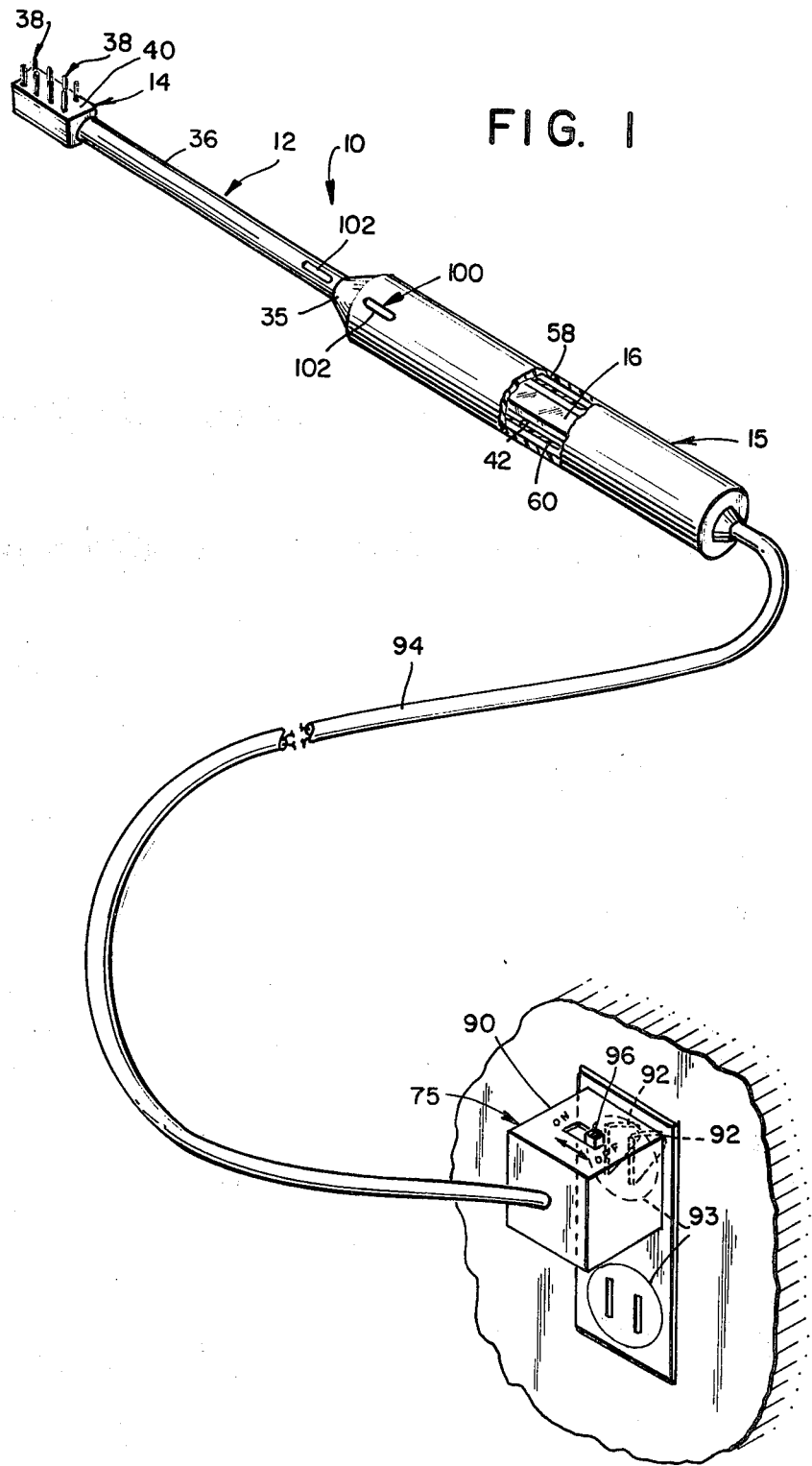
FIG. 1 is a perspective view of an ultrasonic toothbrush in accordance with the present invention.

Referring to the drawings, there is illustrated in FIGS. 1 through 5 a vibratory toothbrush 10 adapted for personal dental hygiene usage by the consumer which is constructed in a manner that includes an elongated member 12 having a brush member 14 at one end thereof with the elongated member 12 adapted to be removably received within the casing 15.

The elongated member 12 may be formed at least in part of a piezoelectric member 16 having an inner end 18 and an outer end 20 with a pair of contacting surfaces 21 and 22 intermediate the respective ends 18 and 20. The contacting surfaces 21 and 22 contain a coating 24 of electrical conductive material well known in the art which, when a current is transmitted to each of the respective contacting surfaces 21 and 22, vibrations will be induced within the member 16 in a longitudinal mode, as illustrated by doubled headed arrow 25.

It is appreciated that the vibration of the piezoelectric member 16 may occur such that the arrow 25 may exhibit torsional as well as longitudinal motion or torsional alone. The elongated member 12 may include a rear end 26 and a front end 28. The cross sectional area of the rear end 26 may be greater than the front end 28 such that the elongated member 12 acts as an acoustic impedance transformer for amplifying vibrations provided by the piezoelectric member 16 in a manner well known in the art.

The structure of the apparatus 10 permits the ready interchangeability of each elongated member 12 with the casing 15 for the reason that each member of the family should use a different brush member 14. Furthermore, the bristles 37, when a brush member 14 is properly used, will have a life expectancy that is much shorter than the apparatus 10. Accordingly, provision has been made for the quick and easy interchangeability of the elongated member 12 within the casing 15. The casing 15 is adapted to be held in the hand of the user and is of a length at least equal to, but generally greater than, that of the member 16. The casing 15 includes an elongated bore 42 adapted to receive the member 16 therein. The casing 15 is spaced from the member 16 over substantially its entire length and is in contacting relationship to the elongated member 12 at a point along the length thereof at which a node of longitudinal vibration occurs.

The casing 15 also partially encloses the elongated member 12 in spaced relation thereto, and sealing means 45 is provided in the bore 42 to engage the elongated member 12 in readily releasable and in a fluid-tight fashion along which a node of longitudinal motion occurs.

The casing 15 is formed from a non-magnetic material and is provided with a rear end 46 remote from the brush member 14 with a passageway 50 adapted to receive wires 51 and 52 in the casing 15 for connection to electrical contact means 55. The sealing means 45 may be in the form of an O-ring 56 mounted on the elongated member 12 in a circular or peripherally extending well 57. The O-ring 56 is adapted to engage the bore 42 to obtain the fluid-tight connection therebetween adjacent to the front end 47 of the casing 15.

The elongated member 12 includes a body portion 30 intermediate the ends 26 and 28 and may be fabricated from a plastic material having acoustic properties for proper vibratory transmission. The rear end 26 may include a well or a seat 32 adapted to receive the end 18 of the piezoelectric member 16 therein and secured thereto by a bonding element or means 34 which may be in the form of an adhesive as the connecting means.

In this manner the member 16 may be readily secured to the body portion 30 to form the elongated member 12 in a simple and economical manner. The body portion 30 may include an enlarged tapered section 35 terminating at the rear end 26 and an elongated forward section 36 terminating at the front end 28. The configuration between the sections 35 and 36 determines the amplitude magnification thereof.

The brush member 14 is adapted to be received within the human mouth and moved across the gingival surface and extends from one end of the elongated member 12. The brush member 14 may be separately fabricated and secured to the forward section 36 or integrally formed therewith. The plurality of bristles or bristle clusters 38 extend outwardly from the face 40 of the brush member 14. The bristle clusters 38 are secured in place in a manner well known in the art in order to assure proper transmission of the mechanical vibrations illustrated by arrow 25 to the respective bristles 37 of each cluster 38. Accordingly, the assembly of the elongated member 12 and brush member 14 may be interchangeable with the casing 15 as hereinafter explained in greater detail. In this manner the assembly 10 may include four members 12 for each family when sold commercially.

The casing 15 may include an outer casing member 58 and an inner casing member 60 having the bore 42 extending therethrough. The inner casing member 60 may extend in telescopic relation with the outer casing member 58 for retainment of the contact means 55 therein. Mounting means 62 is provided for retaining the inner casing 60 within the outer casing 58 in fixed position thereto. The mounting means 62 may include radial or circumferentially extending spaces 64 along the length of the casing members 58 and 60.

The wires 51 and 52 may extend intermediate the casings 58 and 60 and be connected at one end to the electrical contact means 55. The electrical contact means 55 is designed to be mounted within the casing 15 for releasable engagement with the contacting surfaces 21 and 22 so as to obtain instantaneous electrical contact upon the insertion of the elongated member 12 within the bore 42 and disengaged electrical contact upon removal from the bore 42 of the elongated member 12.

Figure 2:
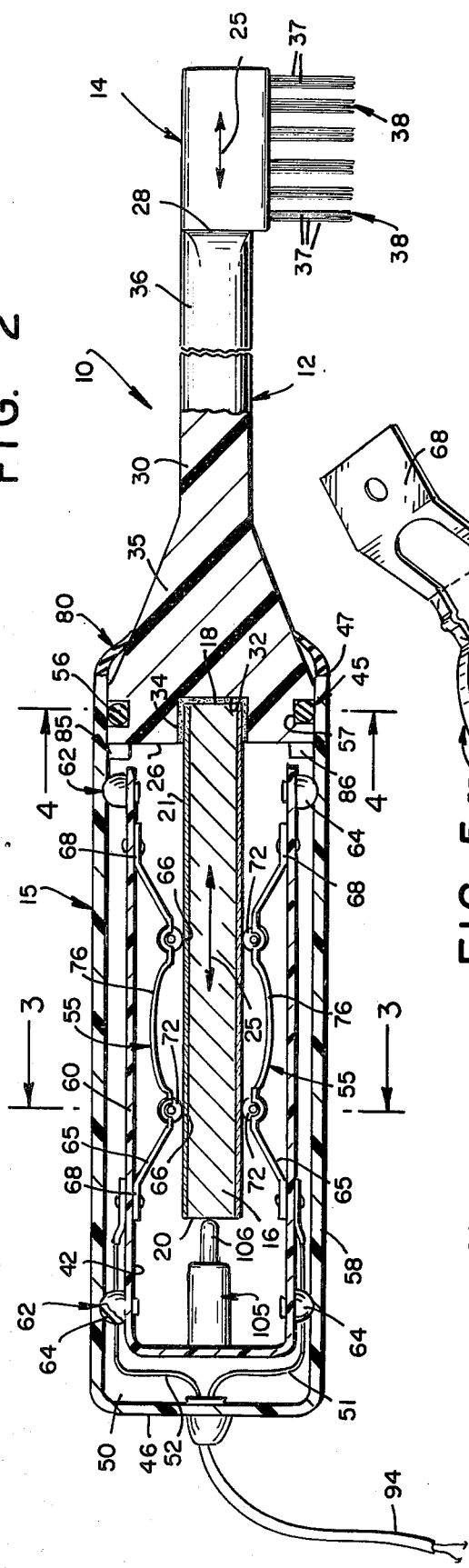
FIG. 2 is an assembled view, in cross section, of the ultrasonic toothbrush according to the present invention.
Figure 4:
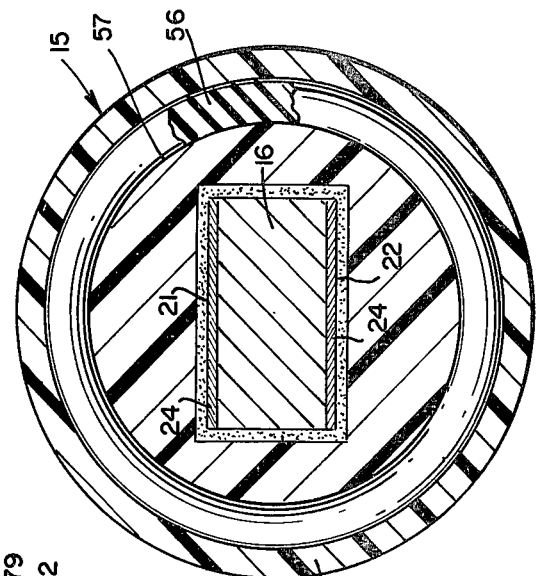
FIG. 4 is a cross-sectional view taken along lines 4—4 of FIG. 2.
Figure 5:
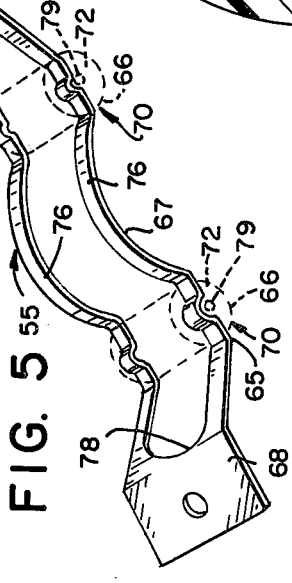
FIG. 5 is a perspective view of the electrical contact means for providing electrical energy to the removable brush assembly.
Figure 3:
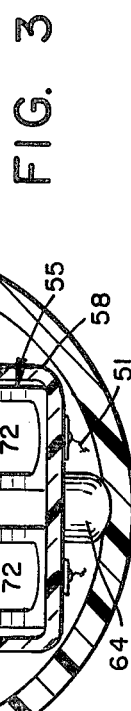
FIG. 3 is a cross-sectional view taken along lines 3—3 of FIG. 2.

The contact means 55 may include a pair of oppositely disposed contact members 65 fabricated from a metallic material and mounted within the bore 42, as illustrated in FIG. 2. Each contact member 65 includes a coupling surface 66 that may be selectively contoured for engagement with a respective one of the contacting surfaces 21 or 22, as illustrated in FIG. 5. The coupling surface 66 may be formed on each contact member 65 and two of which may be provided for use with each surface 21 or 22.

Each contact member 65 includes a body portion 67 and an arm 68 extending from each end of the body portion 67 and rigidly coupled to the inner casing member 60 of the casing 15. To facilitate the ease of the insertion and removal, since children as well as adults will be using the apparatus 10, friction reduction means 70 may be provided and operatively associated with each one of the contact members 65. The friction reduction means 70 may include at least one roller 72 mounted on each one of the contact members 65 and fabricated from a metallic material to maintain electrical transmission between the generating means 75 and the piezoelectric member 16. The body portion 67 may include a pair of flanges 76 with an opening 78 therebetween, and each roller 72 is mounted in a plane perpendicular to the axis of the bore 42 within the opening 78. Each roller 72 may include a shaft 79 coupled to the flanges 76 at each end thereof.

The apparatus 10 may further include shield means 80 at the forward end 47 of the casing 15 so as to circumferentially engage the elongated member 12 for preventing liquid from entering the casing 15. The shield means 80 is flexible and readily adapts to the configuration of the elongated member 12. The shield means 80 may be used in conjunction with the sealing means 45 to provide further security for the prevention of water or other liquids from entering the casing 15.

In order to limit the longitudinal movement that the elongated member 12 is inserted within the casing 15, there may be provided stop means 85 within the bore 42 to limit the axial movement. The stop means 85 may include a shoulder 86 within the bore 42 at a desired location therein. As illustrated in FIG. 2, the rear end 26 abuts against the shoulder 86 to stop the rearward travel of the elongated member 12.

The generating means 75 is used to supply alternating electrical signals to the contact means 55 to establish an alternating field for transmission from the contact means 55 through the respective contact member 65 to the piezoelectric member 16. In this manner mechanical vibrations in the direction of double headed arrow 25 are obtained at the frequency at which the alternating signals are induced in the elongated member 12, and in turn the brush member 14 and the respective bristle clusters 38.

The generating means 75 may be in the form well known in the prior art and the components thereof may be housed in a housing 90 with a pair of electrical prongs 92 extending therefrom and adapted to be plugged into a wall outlet 93, as illustrated in FIG. 1, for powering same. The cable 94 may extend between the housing 90 and plug 95. The generating means 75 may include switch means 96 adapted to be engaged by the user in either an ON or an OFF position.

In order to assist the user in the ready insertion and removal such that the proper orientation of the elongated member 12 with respect to the casing 15 is always attained, there may be utilized guide means 100 so as to assure this correct positionment so that proper engagement between the contacting surfaces 21 and 22. The guide means 100 may include indicia 102 on the elongated member 12 as well as the casing 15 for visual orientation. The guide means may further include, or in the alternative consist of other mechanisms to provide for the positive positioning of the surfaces 21 and 22 which are generally flat and elongated in proper orientation to the contact means 55 as described above.

Accordingly, the user by proper insertion of the elongated member 12 within the casing 15 immediately obtains electrical energy to be transmitted via the contact means 55. In this manner the apparatus 10 is ready for use. If desired, a safety switch may be provided within the casing 15 which is only activated when the elongated member 12 reaches the position provided for by the stop means 85. In this manner, notwithstanding the fact that the switch means 96 is activated, there will be no danger of energizing the apparatus 10 without an elongated member 12 being positioned therein. A form of safety switch means 105 is illustrated in FIG. 2 and may be electrically connected in a conventional manner. The safety switch means 105 includes a protrusion 106 which when engaged by the rear end 20 of member 16 and depressed a certain amount will close the electrical circuit of the generating means 75. The toothbrush may operate in a range of 1,000 to 100,000 cycles per second and preferably in the range of 15,000 to 40,000 cycles per second.

Prior to the present invention it was necessary to permanently solder electrical leads to a crystal element made from a piezoelectric material. This prevented quick interchangeability in that the motor always remained a fixed part of the overall unit that it formed. The present invention permits the piezoelectric member 16 to have no permanent leads secured thereto, such that interchangeability for different members of the household may readily take place. As described above, electrical contact is made on two surfaces of the element 16 upon insertion. It is appreciated that the element 16 may be encapsulated with a coating and only a small area thereof open for electrical coupling by the contact means 55. This would avoid possible wetting of the element 16 before or after use of the apparatus 10.

Although an illustrative embodiment of the invention has been described in detail herein with reference to the accompanying drawings, it is to be understood that the invention is not limited to the precise embodiment, and that various changes and modifications may be effected therein without departing from the scope or spirit of the invention.

What is claimed is:

1. Apparatus for use in personal dental hygiene care comprising:
   A. an elongated member formed at least in part of a piezoelectric member with a pair of contacting surfaces intermediate the respective ends thereof,
   B. a brush member adapted to be received within the human mouth and moved across tooth and gingival surfaces and extending from one end of said elongated member,
   C. a casing adapted to be held in the hand and of a length at least equal to said piezoelectric member and having an elongated bore adapted to receive said piezoelectric member of said elongated member,
   D. sealing means in said bore to engage said elongated member in readily releasable and in a fluid-tight fashion,
   E. electrical contact means contained in said casing for releasable engagement with said contacting surfaces of said piezoelectric member of said elongated member, so as to obtain electrical contact upon the insertion of said elongated member within said bore and disengagement of said electrical contact means upon removal from said bore of said elongated member, and
   F. generating means to supply alternating electrical signals to said contact means to establish an alternating field for transmission from said contact means to said piezoelectric member, whereby mechanical vibrations at the frequency of said alternating signals are induced in said elongated member and said brush member.

2. Apparatus as defined in claim 1, wherein said casing encloses said piezoelectric member over substantially its entire length.

3. Apparatus as defined in claim 2, wherein a fluid-tight seal is provided between said casing and said elongated member by said sealing means at a point along said elongated member at which a node of longitudinal motion occurs.

4. Apparatus as defined in claim 3, wherein said casing is formed of a non-magnetic material and is provided at its end remote from said brush member with a passageway adapted to receive wires in said casing for connection to said contact means.

5. Apparatus as defined in claim 1, wherein said elongated member comprises an acoustic impedance transformer for amplifying vibrations provided by said piezoelectric member.

6. Apparatus as defined in claim 1, including guide means to provide an indication for the user as to the correct positioning of said elongated member within said bore to obtain proper engagement between said contacting surfaces and said contact means.

7. Apparatus as defined in claim 6, wherein said guide means includes indicia on said elongated member and said casing.

8. Apparatus as defined in claim 7, wherein said indicia includes a colored mark on said casing and said elongated member to obtain said alignment.

9. Apparatus as defined in claim 1, wherein said contact means includes a pair of oppositely disposed contact members mounted in said bore, and each said contact member having a coupling surface for engagement with one of said contacting surfaces.

10. Apparatus as defined in claim 9, wherein each one of said contact members includes:
    a. a body portion, and
    b. an arm extending from each end of said body portion and rigidly coupled to said casing.

11. Apparatus as defined in claim 9, including friction reduction means operatively associated with each one of said contact members so as to facilitate the insertion and removal of said elongated member within said bore.

12. Apparatus as defined in claim 11, wherein said friction reduction means includes at least one metallic roller mounted on each one of said contact members to maintain electrical transmission between said generating means and said piezoelectric member.

13. Apparatus as defined in claim 12, wherein said body portion includes a pair of flanges with an opening therebetween and said roller is mounted in a plane perpendicular to the axis of said bore within said opening.

14. Apparatus as defined in claim 13, wherein said roller includes a shaft coupled to said flanges at each end thereof.

15. Apparatus as defined in claim 1, including shield means at one end of said casing so as to circumferentially engage said elongated member for preventing liquid from entering said casing.

16. Apparatus as defined in claim 15, wherein said shield means is flexible to adapt to the configuration of said elongated member.

17. Apparatus as defined in claim 1, wherein said casing includes:
   a. an outer-casing member,
   b. an inner casing member adapted to extend in telescopic relation within said outer casing for retainment of said contact means thereon, and
   c. mounting means for retaining said inner casing within said outer casing in fixed position thereto.

18. Apparatus as defined in claim 17, including wires extending from said generating means intermediate said outer casing and said inner casing and connected to said contact means.

19. Apparatus as defined in claim 17, wherein a two pair of said contact means is provided.

20. Apparatus as defined in claim 1, wherein said sealing means includes an O-ring mounted on said elongated member for engagement with said bore to obtain the fluid-tight integrity of the apparatus.

21. Apparatus as defined in claim 1, including stop means within said bore to limit the axial movement of said elongated member within said casing.

22. Apparatus as defined in claim 21, said stop means including a shoulder within said bore.

23. Apparatus as defined in claim 1, wherein said generating means is contained in a housing with a pair of electrical prongs extending therefrom and adapted to be plugged into a wall outlet for powering same.

24. Apparatus as defined in claim 3, wherein said generating means includes switch means adapted to be engaged by a user for powering same.

25. Apparatus as defined in claim 1, wherein said brush member and said elongated member are integrally formed and fabricated from a plastic material.

26. Apparatus as defined in claim 1, including connecting means to rigidly join said piezoelectric member to one end of said elongated member.

27. Apparatus as defined in claim 1, including safety switch means which permits energization of said contact means only when said elongated member is properly positioned within said casing.

28. Apparatus as defined in claim 27, wherein said safety switch means is mounted within said casing for engagement by said piezoelectric member.

* * * * *